(12) United States Patent
Wallace et al.

(10) Patent No.: US 8,019,441 B2
(45) Date of Patent: Sep. 13, 2011

(54) COLLAPSIBLE/EXPANDABLE TUBULAR ELECTRODE LEADS

(75) Inventors: Michael P. Wallace, Fremont, CA (US); Robert J. Garabedian, Mountain View, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1116 days.

(21) Appl. No.: 11/459,618

(22) Filed: Jul. 24, 2006

(65) Prior Publication Data
US 2006/0259110 A1    Nov. 16, 2006

Related U.S. Application Data

(63) Continuation of application No. 10/799,295, filed on Mar. 12, 2004, now abandoned.

(51) Int. Cl.
*A61N 1/05* (2006.01)
(52) U.S. Cl. ........................................................ 607/117
(58) Field of Classification Search ........... 607/116–118
See application file for complete search history.

(56) References Cited

U.S. PATENT DOCUMENTS

| | | | |
|---|---|---|---|
| 538,514 A | 4/1895 | Haeseler | |
| 661,046 A | 11/1900 | Graves | |
| 4,141,365 A | 2/1979 | Fischell et al. | |
| 4,285,347 A | 8/1981 | Hess | |
| 4,519,403 A | 5/1985 | Dickhudt | |
| 4,608,985 A | 9/1986 | Crish et al. | |
| 4,658,835 A | 4/1987 | Pohndorf | |
| 4,739,768 A | 4/1988 | Engelson | |
| 4,813,934 A | 3/1989 | Engelson et al. | |
| 4,869,255 A | 9/1989 | Putz | |
| 4,884,579 A | 12/1989 | Engelson | |
| 5,005,587 A | 4/1991 | Scott | |
| 5,010,894 A | 4/1991 | Edhag | |
| 5,010,895 A | 4/1991 | Maurer et al. | |

(Continued)

FOREIGN PATENT DOCUMENTS

EP        0 861 676        9/1998

(Continued)

OTHER PUBLICATIONS

Office Action dated Apr. 16, 2008 for related U.S. Appl. No. 10/799,271, filed Mar. 12, 2004, Inventor: Robert J. Garabedian (22 pages).

(Continued)

*Primary Examiner* — George R. Evanisko
(74) *Attorney, Agent, or Firm* — Vista IP Law Group LLP

(57) ABSTRACT

A medical lead and method of treating a patient are provided. The medical lead comprises an electrically insulative tubular membrane, a resilient spring element associated with the insulative membrane, and at least one electrode associated with the insulative membrane. The medical lead is configured to be collapsed into a compact form for percutaneous delivery into the patient, thereby obviating the need to perform an invasive surgical procedure on the patient. The body formed by these elements, when expanded, can be sized to fit within the epidural space of a patient. The patient can be treated by placing the medical lead into a collapsed state by applying a compressive force to the medical lead, percutaneously delivering the collapsed medical lead into the patient adjacent tissue to be treated, and placing the medical lead into an expanded state by releasing the compressive force. In one preferred method, the stimulation lead is used to stimulate tissue, such as spinal cord tissue.

19 Claims, 8 Drawing Sheets

U.S. PATENT DOCUMENTS

| | | | |
|---|---|---|---|
| 5,107,856 A | 4/1992 | Kristiansen et al. |
| 5,170,802 A | 12/1992 | Mehra |
| 5,224,491 A | 7/1993 | Mehra |
| 5,234,437 A | 8/1993 | Sepetka |
| 5,239,999 A | 8/1993 | Imran |
| 5,250,071 A | 10/1993 | Palermo |
| 5,261,916 A | 11/1993 | Engelson |
| 5,263,488 A | 11/1993 | Van Veen et al. |
| 5,304,195 A | 4/1994 | Twyford, Jr. et al. |
| 5,306,272 A | 4/1994 | Cohen et al. |
| 5,312,415 A | 5/1994 | Palermo |
| 5,342,410 A | 8/1994 | Braverman |
| 5,350,397 A | 9/1994 | Palermo et al. |
| 5,358,514 A | 10/1994 | Schulman et al. |
| 5,365,926 A | 11/1994 | Desai |
| 5,374,285 A | 12/1994 | Vaiani et al. |
| 5,385,528 A * | 1/1995 | Wilk ................................ 600/18 |
| 5,391,200 A | 2/1995 | KenKnight et al. |
| 5,397,341 A | 3/1995 | Hirschberg et al. |
| 5,411,551 A | 5/1995 | Winston et al. |
| 5,417,719 A | 5/1995 | Hull et al. |
| 5,423,864 A | 6/1995 | Ljungstroem |
| 5,423,877 A | 6/1995 | Mackey |
| 5,443,492 A | 8/1995 | Stokes et al. |
| 5,462,545 A | 10/1995 | Wang et al. |
| 5,464,446 A | 11/1995 | Dreessen et al. |
| 5,501,703 A | 3/1996 | Holsheimer et al. |
| 5,509,411 A | 4/1996 | Littmann et al. |
| 5,531,779 A | 7/1996 | Dahl et al. |
| 5,534,007 A | 7/1996 | St. Germain et al. |
| 5,543,864 A | 8/1996 | Hirschman et al. |
| 5,582,609 A | 12/1996 | Swanson et al. |
| 5,603,731 A | 2/1997 | Whitney |
| 5,611,345 A | 3/1997 | Hibbeln |
| 5,647,870 A | 7/1997 | Kordis et al. |
| 5,683,422 A | 11/1997 | Rise |
| 5,702,438 A | 12/1997 | Avitali |
| 5,707,354 A | 1/1998 | Salmon et al. |
| 5,713,922 A | 2/1998 | King |
| 5,716,377 A | 2/1998 | Rise et al. |
| 5,752,979 A | 5/1998 | Benabid |
| 5,755,750 A | 5/1998 | Petruska et al. |
| 5,782,239 A | 7/1998 | Webster, Jr. et al. |
| 5,782,798 A | 7/1998 | Rise |
| 5,792,187 A | 8/1998 | Adams |
| 5,800,474 A | 9/1998 | Benabid et al. |
| 5,814,062 A | 9/1998 | Sepetka et al. |
| 5,833,709 A | 11/1998 | Rise et al. |
| 5,846,196 A * | 12/1998 | Siekmeyer et al. ............ 600/374 |
| 5,846,238 A | 12/1998 | Jackson et al. |
| 5,860,974 A | 1/1999 | Abele |
| 5,871,483 A | 2/1999 | Jackson et al. |
| 5,891,136 A | 4/1999 | McGee et al. |
| 5,902,236 A * | 5/1999 | Iversen ....................... 623/23.65 |
| 5,902,331 A | 5/1999 | Bonner et al. |
| 5,908,385 A | 6/1999 | Chechelski et al. |
| 5,925,070 A | 7/1999 | King et al. |
| 5,928,278 A | 7/1999 | Kitschmann |
| 5,931,862 A | 8/1999 | Carson |
| 5,938,689 A | 8/1999 | Fischell et al. |
| 5,954,761 A | 9/1999 | Machek et al. |
| 5,967,986 A | 10/1999 | Cimochowski et al. |
| 5,984,909 A | 11/1999 | Lurie et al. |
| 6,002,964 A | 12/1999 | Feler et al. |
| 6,006,124 A | 12/1999 | Fischell et al. |
| 6,006,134 A | 12/1999 | Hill et al. |
| 6,015,387 A | 1/2000 | Schwartz et al. |
| 6,016,449 A | 1/2000 | Fischell et al. |
| 6,018,682 A | 1/2000 | Rise |
| 6,027,456 A | 2/2000 | Feler et al. |
| 6,036,689 A | 3/2000 | Tu et al. |
| 6,053,873 A | 4/2000 | Govari et al. |
| 6,066,163 A | 5/2000 | John |
| 6,074,407 A | 6/2000 | Levine et al. |
| 6,074,507 A | 6/2000 | Sukenik |
| 6,091,980 A | 7/2000 | Squire et al. |
| 6,094,596 A | 7/2000 | Morgan |
| 6,119,044 A | 9/2000 | Kuzma |
| 6,122,548 A | 9/2000 | Starkebaum et al. |
| 6,128,537 A | 10/2000 | Rise |
| 6,128,538 A | 10/2000 | Fischell et al. |
| 6,136,021 A | 10/2000 | Tockman et al. |
| 6,141,576 A | 10/2000 | Littmann et al. |
| 6,152,899 A | 11/2000 | Farley et al. |
| 6,161,029 A | 12/2000 | Spreigl et al. |
| 6,161,047 A | 12/2000 | King et al. |
| 6,170,488 B1 | 1/2001 | Spillman, Jr. et al. |
| 6,179,858 B1 | 1/2001 | Squire et al. |
| 6,192,279 B1 | 2/2001 | Barreras, Sr. et al. |
| 6,192,280 B1 | 2/2001 | Sommer et al. |
| 6,205,361 B1 | 3/2001 | Kuzma et al. |
| 6,216,045 B1 | 4/2001 | Black et al. |
| 6,231,516 B1 | 5/2001 | Keilman et al. |
| 6,249,707 B1 | 6/2001 | Kohnen et al. |
| 6,263,248 B1 | 7/2001 | Farley et al. |
| 6,266,568 B1 | 7/2001 | Mann et al. |
| 6,292,702 B1 | 9/2001 | King et al. |
| 6,319,241 B1 | 11/2001 | King et al. |
| 6,319,251 B1 | 11/2001 | Tu et al. |
| 6,330,477 B1 | 12/2001 | Casavant |
| 6,353,762 B1 | 3/2002 | Baudino et al. |
| 6,360,122 B1 | 3/2002 | Fischell et al. |
| 6,361,528 B1 | 3/2002 | Wilson et al. |
| 6,370,427 B1 | 4/2002 | Alt et al. |
| 6,391,052 B2 | 5/2002 | Buirge et al. |
| 6,391,643 B1 | 5/2002 | Chen et al. |
| 6,393,325 B1 | 5/2002 | Mann et al. |
| 6,397,109 B1 | 5/2002 | Cammilli et al. |
| 6,402,746 B1 | 6/2002 | Whayne et al. |
| 6,408,214 B1 | 6/2002 | Williams et al. |
| 6,415,187 B1 | 7/2002 | Kuzma et al. |
| 6,418,344 B1 | 7/2002 | Rezai et al. |
| 6,430,442 B1 | 8/2002 | Peters et al. |
| 6,438,427 B1 | 8/2002 | Rexhausen et al. |
| 6,442,413 B1 | 8/2002 | Silver |
| 6,442,435 B2 * | 8/2002 | King et al. ..................... 607/117 |
| 6,445,953 B1 | 9/2002 | Bulkes et al. |
| 6,463,328 B1 | 10/2002 | John |
| 6,466,822 B1 | 10/2002 | Pless |
| 6,480,743 B1 | 11/2002 | Kirkpatrick et al. |
| 6,484,059 B2 | 11/2002 | Gielen |
| 6,510,347 B2 | 1/2003 | Borkan |
| 6,516,227 B1 | 2/2003 | Meadows et al. |
| 6,519,488 B2 | 2/2003 | KenKnight et al. |
| 6,522,932 B1 * | 2/2003 | Kuzma et al. .................. 607/116 |
| 6,529,774 B1 | 3/2003 | Greene |
| 6,539,283 B2 | 3/2003 | Takagi |
| 6,547,788 B1 | 4/2003 | Maguire et al. |
| 6,547,870 B1 | 4/2003 | Griessmann et al. |
| 6,562,063 B1 | 5/2003 | Euteneuer et al. |
| 6,584,358 B2 | 6/2003 | Carter et al. |
| 6,587,733 B1 | 7/2003 | Cross, Jr. et al. |
| 6,589,230 B2 | 7/2003 | Gia et al. |
| 6,591,138 B1 | 7/2003 | Fischell et al. |
| 6,597,953 B2 | 7/2003 | Boling |
| 6,600,954 B2 | 7/2003 | Cohen et al. |
| 6,600,956 B2 | 7/2003 | Maschino et al. |
| 6,606,521 B2 | 8/2003 | Paspa et al. |
| 6,625,496 B1 | 9/2003 | Ollivier |
| 6,647,296 B2 | 11/2003 | Fischell et al. |
| 6,658,302 B1 | 12/2003 | Kuzma et al. |
| 6,662,055 B1 | 12/2003 | Prutchi |
| 6,665,562 B2 | 12/2003 | Gluckman et al. |
| 6,671,544 B2 | 12/2003 | Baudino |
| 6,675,046 B2 | 1/2004 | Holsheimer |
| 6,690,974 B2 | 2/2004 | Archer et al. |
| 6,697,676 B2 | 2/2004 | Dahl et al. |
| 6,714,822 B2 | 3/2004 | King et al. |
| 6,837,886 B2 | 1/2005 | Collins et al. |
| 6,842,648 B2 | 1/2005 | Partridge et al. |
| 6,895,283 B2 | 5/2005 | Erickson et al. |
| 6,909,918 B2 | 6/2005 | Stypulkowski |
| 6,959,820 B2 | 11/2005 | Koslow |
| 6,988,007 B1 | 1/2006 | Morgan et al. |
| 6,999,820 B2 | 2/2006 | Jordan |
| 7,072,719 B2 | 7/2006 | Vinup et al. |
| 7,177,702 B2 | 2/2007 | Wallace et al. |

| | | | |
|---|---|---|---|
| 7,231,260 B2 | 6/2007 | Wallace et al. | |
| 7,349,743 B2 | 3/2008 | Tadlock | |
| 7,561,924 B2 | 7/2009 | Kolberg et al. | |
| 7,590,454 B2 | 9/2009 | Garabedian et al. | |
| 2001/0025192 A1 | 9/2001 | Gerber et al. | |
| 2001/0041821 A1* | 11/2001 | Wilk | 600/16 |
| 2001/0053885 A1 | 12/2001 | Gielen et al. | |
| 2002/0026228 A1 | 2/2002 | Schauerte | |
| 2002/0111661 A1 | 8/2002 | Cross et al. | |
| 2002/0151948 A1 | 10/2002 | King et al. | |
| 2002/0151949 A1 | 10/2002 | Dahl et al. | |
| 2002/0156513 A1 | 10/2002 | Borkan | |
| 2002/0183791 A1 | 12/2002 | Denker et al. | |
| 2002/0188207 A1 | 12/2002 | Richter | |
| 2003/0014016 A1 | 1/2003 | Purdy | |
| 2003/0040785 A1 | 2/2003 | Maschino et al. | |
| 2003/0097051 A1 | 5/2003 | Kolberg et al. | |
| 2003/0199962 A1 | 10/2003 | Struble et al. | |
| 2003/0204135 A1 | 10/2003 | Bystritsky | |
| 2003/0204228 A1 | 10/2003 | Cross, Jr. et al. | |
| 2004/0015193 A1 | 1/2004 | Lamson et al. | |
| 2004/0098074 A1* | 5/2004 | Erickson et al. | 607/117 |
| 2005/0004639 A1 | 1/2005 | Erickson | |
| 2005/0137646 A1 | 6/2005 | Wallace et al. | |
| 2005/0149156 A1 | 7/2005 | Libbus et al. | |
| 2005/0203599 A1 | 9/2005 | Garabedian et al. | |
| 2005/0203600 A1 | 9/2005 | Wallace et al. | |
| 2005/0203602 A1 | 9/2005 | Wallace et al. | |
| 2005/0251238 A1 | 11/2005 | Wallace et al. | |
| 2005/0251239 A1 | 11/2005 | Wallace et al. | |
| 2006/0129203 A1 | 6/2006 | Garabedian et al. | |
| 2006/0161246 A1 | 7/2006 | Rhim et al. | |

FOREIGN PATENT DOCUMENTS

| | | |
|---|---|---|
| EP | 0 865 800 A2 | 9/1998 |
| EP | 0 865 800 A3 | 12/1999 |
| EP | 0 864 800 B1 | 9/2004 |
| WO | WO 01/85094 | 11/2001 |
| WO | WO 03/077986 | 9/2003 |

OTHER PUBLICATIONS

Canavero, Sergio at al., "Extradural Motor Cortex Stimulation for Advanced Parkinson Disease," J. Neurosurg. 97: pp. 1208-1211, 2002.
Kunieda, Takeharu at al., "Use of Cavernous Sinus EEG in the Detection of Seizure Onset and Spread in Mesial Temporal Lobe Epilepsy," Epilepsia, 41(11): pp. 1411-1419, 2000.
Onal, Cagatay, "Complications of Invasive Subdural Grid Monitoring in Children with Epilepsy," J. Neurosurg. 98: pp. 1017-1026, 2003.
PCT International Search Report for PCT/US2005/006569, Applicant: Boston Scientific Scimed, Inc., Forms PCT/ISA 210 and 220, dated Jun. 13, 2005 (7 pages).
PCT Written Opinion of the International Search Authority for PCT/US2005/006569, Applicant: Boston Scientific Scimed, Inc., Form PCT/ISA/237, dated Jun. 13, 2005 (5 pages).
PCT International Search Report for PCT/US2005/010121, Applicant: Boston Scientific Scimed, Inc., Forms PCT/ISA/210 and 220, dated Jul. 4, 2005 (7 pages).
PCT Written Opinion of the International Search Authority for PCT/US2005/010121, Applicant: Boston Scientific Scimed, Inc., Form PCT/ISA/237, dated Jul. 4, 2005 (5 pages).
Web Article: IP.com: "Dual Lumen Inflatable Lead." File://c:\unzipped\IPCOM000019703D1\0_properties.xml, Published Sep. 25, 2003 (7 pages).
Web Article: IP.com: "Electrode Design to Stimulate Blood Vessels, Nerves, or Other Tubular Organs." File://c:\unzipped\IPCOM000010247D1\0_properties.xml, Published Nov. 13, 2002 (13 pages).
Web Article: IP.com: "Epidural Needle for Spinal Cord Stimulation Electrode." File://c:\unzipped\IPCOM000011384D1\0_properties.xml, Published Feb. 14, 2003 (6 pages).
Web Article: IP.com: "Medical Lead System and Method for Insertion into the Spinal Cord." File://c:\unzipped\IPCOM000011389D1\0_properties.xml, Published Feb. 17, 2003 (7 pages).
Web Article: IP.com: "Methods and Placement of Neurostimulation Lead, Infusion Catheter, and/or Sensor Via the Vasculature to the Brain." IPCOM000012135D, Published Apr. 10, 2003 (11 pages).
Web Article: IP.com: "Methods of Placement of Neurostimulation Lead, Infusion Catheter, and/or Sensor Via Peripheral Vasculature." 0349945-003. (7 pages).
Web Article: IP.com: "Skull-Mounted Electrical Stimulation System." File://c:\unzipped\IPCOM000019827D1\0_properties.xml, Published Oct. 1, 2003 (29 pages).
Web Article: IP.com: "Skull-Mounted Electrical Stimulation System and Method for Treating Patients." File://c:\unzipped\IPCOM000021554D1\0_properties.xml, Published Jan. 22, 2004 (31 pages).
Web Article: IP.com: "Spinal Cord Stimulation as a Therapy for Epilepsy." File://c:\unzipped\IPCOM000019881D1\0_properties.xml, Published Oct. 6, 2003 (10 pages).
Web Article: IP.com: "System and Method for Lead Fixation." File://c:\unzipped\IPCOM000019571D1\0_properties.xml, Published Oct. 19, 2003 (11 pages).
Web Article: IP.com: "Transcutaneous Screening Test for Evaluation of Potential Efficacy of Chronic Trigeminal Neurostimulation as a Therapy for Epilepsy." File://c:\unzippe\IPCOM000011987D1\0_properties.xml, Published Mar. 28, 2003 (8 pages).
Office Action dated Aug. 30, 2007 for related European Patent Application No. 05 733 553.1-1265, Applicant: Boston Scientific Limited (4 pages).
Advisory Action dated Aug. 11, 2006 for this file U.S. Appl. No. 10/841,069, Inventor: Michael P. Wallace et al. (3 pages).
Advisory Action dated Sep. 13, 2006 for this file U.S. Appl. No. 10/841,069, Inventor: Michael P. Wallace et al. (3 pages).
Advisory Action dated Dec. 6, 2006 for this file U.S. Appl. No. 10/841,069, Inventor: Michael P. Wallace et al. (4 pages).
Non-Final Office Action dated Jun. 15, 2007 for this file U.S. Appl. No. 10/841,069, Inventor: Michael P. Wallace et al. (7 pages).
Office Action dated Oct. 31, 2006 for related U.S. Appl. No. 10/841,070, Inventor: Michael Wallace (9 pages).
Office Action dated Jun. 26, 2007 for related U.S. Appl. No. 10/799,271, Inventor: Robert J. Garabedian et al. (9 pages).
Final Office Action dated Nov. 5, 2007 for related U.S. Appl. No. 10/799,271, Inventor: Robert J. Garabedian (7 pages).
Office Action dated Apr. 10, 2007 for related U.S. Appl. No. 11/010,232, Inventor: Robert J. Garabedian et al. (9 pages).
Final Office Action dated Aug. 22, 2007 for related U.S. Appl. No. 11/010,232, Inventor: Robert J. Garabedian et al. (8 pages).
Amendment dated Sep. 4, 2007 for related U.S. Appl. No. 10/841,069, filed May 6, 2004, Inventor: Michael P. Wallace (11 pages).
Office Action dated Mar. 25, 2008 for related U.S. Appl. No. 10/841,069, filed May 6, 2004, Inventor: Michael P. Wallace (10 pages).
Amendment after final dated May 23, 2008 for related U.S. Appl. No. 10/841,069, filed May 6, 2004, Inventor: Michael P. Wallace (8 pages).
Advisory Action dated Jun. 4, 2008 for related U.S. Appl. No. 10/841,069, filed May 6, 2004, Inventor: Michael P. Wallace (6 pages).
Office Action dated Nov. 28, 2008 for related U.S. Appl. No. 10/841,069, filed May 6, 2004, Inventor: Michael P. Wallace (19 pages).
Amendment dated Jan. 27, 2009 for related U.S. Appl. No. 10/841,069, filed May 6, 2004, Inventor: Michael P. Wallace (11 pages).
Advisory Action dated Feb. 10, 2009 for related U.S. Appl. No. 10/841,069, filed May 6, 2004, Inventor: Michael P. Wallace (3 pages).
Amendment dated Feb. 10, 2009 for related U.S. Appl. No. 10/841,069, filed May 6, 2004, Inventor: Michael P. Wallace (1 page).
Amendment dated Feb. 27, 2009 for related U.S. Appl. No. 10/841,069, filed May 6, 2004, Inventor: Michael P. Wallace (15 pages).
Office Action dated May 12, 2009 for related U.S. Appl. No. 10/841,069, filed May 6, 2004, Inventor: Michael P. Wallace (14 pages).

Amendment dated Aug. 12, 2009 for related U.S. Appl. No. 10/841,069, filed May 6, 2004, Inventor: Michael P. Wallace (15 pages).
Office Action dated Dec. 8, 2009 for related U.S. Appl. No. 10/841,069, filed May 6, 2004, Inventor: Michael P. Wallace (14 pages).
Amendment dated Nov. 29, 2006 for related U.S. Appl. No. 10/841,070, filed May 6, 2004, Inventor: Michael P. Wallace (13 pages).
Notice of Allowance dated Jan. 12, 2007 for related U.S. Appl. No. 10/841,070, filed May 6, 2004, Inventor: Michael P. Wallace (6 pages).
Amendment dated Apr. 5, 2007 for related U.S. Appl. No. 10/841,070, filed May 6, 2004, Inventor: Michael P. Wallace (1 page).
Notice of Allowance dated Apr. 5, 2007 for related U.S. Appl. No. 10/841,070, filed May 6, 2004, Inventor: Michael P. Wallace (8 pages).
Amendment dated Jul. 15, 2008 for related U.S. Appl. No. 10/799,271, filed Mar. 12, 2004, Inventor: Robert J. Garabedian (21 pages).
Office Action dated Oct. 21, 2008 for related U.S. Appl. No. 10/799,271, filed Mar. 12, 2004, Inventor: Robert J. Garabedian (9 pages).
Amendment dated Jan. 27, 2009 for related U.S. Appl. No. 10/799,271, filed Mar. 12, 2004, Inventor: Robert J. Garabedian (17 pages).
Notice of Allowance dated May 19, 2009 for related U.S. Appl. No. 10/799,271, filed Mar. 12, 2004, Inventor: Robert J. Garabedian (7 pages).
Amendment dated Oct. 31, 2007 for related U.S. Appl. No. 11/010,232, filed Dec. 10, 2004, Inventor: Robert J. Garabedian (8 pages).
Office Action dated Jan. 8, 2008 for related U.S. Appl. No. 11/010,232, filed Dec. 10, 2004, Inventor: Robert J. Garabedian (18 pages).
Amendment dated Mar. 11, 2008 for related U.S. Appl. No. 11/010,232, filed Dec. 10, 2004, Inventor: Robert J. Garabedian (7 pages).
Office Action dated Jun. 18, 2008 for related U.S. Appl. No. 11/010,232, filed Dec. 10, 2004, Inventor: Robert J. Garabedian (10 pages).
Amendment dated Aug. 14, 2008 for related U.S. Appl. No. 11/010,232, filed Dec. 10, 2004, Inventor: Robert J. Garabedian (10 pages).
Amendment dated Sep. 2, 2008 for related U.S. Appl. No. 11/010,232, filed Dec. 10, 2004, Inventor: Robert J. Garabedian (1 page).
Advisory Action dated Sep. 2, 2008 for related U.S. Appl. No. 11/010,232, filed Dec. 10, 2004, Inventor: Robert J. Garabedian (5 pages).
Office Action dated Feb. 13, 2009 for related U.S. Appl. No. 11/010,232, filed Dec. 10, 2004, Inventor: Robert J. Garabedian (12 pages).
Amendment after final dated Apr. 13, 2009 for related U.S. Appl. No. 11/010,232, filed Dec. 10, 2004, Inventor: Robert J. Garabedian (15 pages).
Amendment dated May 6, 2009 for related U.S. Appl. No. 11/010,232, filed Dec. 10, 2004, Inventor: Robert J. Garabedian (1 page).
Advisory Action dated May 6, 2009 for related U.S. Appl. No. 11/010,232, filed Dec. 10, 2004, Inventor: Robert J. Garabedian (3 pages).
Amendment dated May 18, 2009 for related U.S. Appl. No. 11/010,232, filed Dec. 10, 2004, Inventor: Robert J. Garabedian (15 pages).
Office Action dated Aug. 5, 2009 for related U.S. Appl. No. 11/010,232, filed Dec. 10, 2004, Inventor: Robert J. Garabedian (13 pages).
Amendment dated Nov. 5, 2009 for related U.S. Appl. No. 11/010,232, filed Dec. 10, 2004, Inventor: Robert J. Garabedian (15 pages).
Office Action dated Mar. 2, 2010 for related U.S. Appl. No. 11/010,232, filed Dec. 10, 2004, Inventor: Robert J. Garabedian (12 pages).
Amendment dated Apr. 29, 2010 for related U.S. Appl. No. 11/010,232, filed Dec. 10, 2004, Inventor: Robert J. Garabedian (11 pages).
Office Action dated May 25, 2010 for related U.S. Appl. No. 11/010,232, filed Dec. 10, 2004, Inventor: Robert J. Garabedian (11 pages).
Office Action dated Aug. 23, 2005 for related U.S. Appl. No. 10/799,270, filed Mar. 12, 2004, Inventor: Michael P. Wallace (15 pages).
Amendment dated Nov. 25, 2005 for related U.S. Appl. No. 10/799,270, filed Mar. 12, 2004, Inventor: Michael P. Wallace (14 pages).
Office Action dated Jan. 9, 2006 for related U.S. Appl. No. 10/799,270, filed Mar. 12, 2004, Inventor: Michael P. Wallace (13 pages).
Amendment dated Apr. 5, 2006 for related U.S. Appl. No. 10/799,270, filed Mar. 12, 2004, Inventor: Michael P. Wallace (11 pages).
Office Action dated Jun. 14, 2006 for related U.S. Appl. No. 10/799,270, filed Mar. 12, 2004, Inventor: Michael P. Wallace (5 pages).
Response dated Jul. 11, 2006 for related U.S. Appl. No. 10/799,270, filed Mar. 12, 2004, Inventor: Michael P. Wallace (2 pages).
Notice of Allowance dated Oct. 11, 2008 for related U.S. Appl. No. 10/799,270, filed Mar. 12, 2004, Inventor: Michael P. Wallace (11 pages).
Office Action dated Jul. 12, 2005 for related U.S. Appl. No. 10/799,295, filed Mar. 12, 2004, Inventor: Michael P. Wallace (6 pages).
Amendment dated Aug. 24, 2005 for related U.S. Appl. No. 10/799,295, filed Mar. 12, 2004, Inventor: Michael P. Wallace (7 pages).
Office Action dated Sep. 19, 2005 for related U.S. Appl. No. 10/799,295, filed Mar. 12, 2004, Inventor: Michael P. Wallace (10 pages).
Amendment dated Dec. 12, 2005 for related U.S. Appl. No. 10/799,295, filed Mar. 12, 2004, Inventor: Michael P. Wallace(10 pages).
Office Action dated Mar. 2, 2006 for related U.S. Appl. No. 10/799,295, filed Mar. 12, 2004, Inventor: Michael P. Wallace (10 pages).
Amendment dated May 1, 2006 for related U.S. Appl. No. 10/799,295, filed Mar. 12, 2004, Inventor: Michael P. Wallace (7 pages).
Office Action dated Jul. 5, 2006 for related U.S. Appl. No. 10/799,295, filed Mar. 12, 2004, Inventor: Michael P. Wallace.
Amendment dated Aug. 27, 2009 for related U.S. Appl. No. 12/549,223, filed Aug. 27, 2009, Inventor: Robert J. Garabedian (7 pages).
Extended European Search Report dated Dec. 19, 2008 in EP Application No. 08017295.0-1265; (5 pages).
PCT International Search Report for PCT/US2005/007179, Applicant: Boston Scientific Scimed, Inc., Forms PCT/ISA/210 and 220, Dated Jun. 24, 2005 ( 6 pages).
PCT Written Opinion for PCT/US2005/007179, dated Jun. 24, 2005, Applicant: Boston Scientific Scimed, Inc., Forms PCT/ISA/237, 5 pages).
Non-Final Rejection dated Nov. 2, 2005 in U.S. Appl. No. 10/841,069, filed May 6, 2004, Inventor: Michael P. Wallace, (10 pages).
Final Rejection dated May 4, 2006 in U.S. Appl. No. 10/841,069, filed May 6, 2004, Inventor: Michael P. Wallace, (9 pages).
Appeal Brief dated Jan. 5, 2007 U.S. Appl. No. 10/841,069, filed May 6, 2004, Inventor: Michael P. Wallace, (13 pages).
Appeal Brief dated Apr. 4, 2007 in U.S. Appl. No. 10/841,069, filed May 6, 2004, Inventor: Michael P. Wallace, (14 pages).
Appeal Brief dated Sep. 3, 2008 in U.S. Appl. No. 10/841,069, filed May 6, 2004, Inventor: Michael P. Wallace, (30 pages).
Appeal Brief dated Mar. 25, 2010 in U.S. Appl. No. 10/841,069, filed May 6, 2004, Inventor: Michael P. Wallace, (26 pages).

Examiner's Answers to Appeal Brief dated Jun. 7, 2010 in U.S. Appl. No. 10/841,069, filed May 6, 2004, Inventor: Michael P. Wallace, (15 pages).

Non-Final Rejection dated Jun. 7, 2006 in U.S. Appl. No. 10/841,070, filed May 6, 2004, Inventor: Michael P. Wallace, (13 pages).

Non-Final Rejection dated May 25, 2006 in U.S. Appl. No. 10/799,271, filed Mar. 12, 2004, Inventor: Robert J. Garabedian, (15 pages).

Non-Final Rejection dated Apr. 16, 2008 in U.S. Appl. No. 10/799,271, filed Mar. 12, 2004, Inventor: Robert J. Garabedian, (22 pages).

Advisory Action dated Jul. 30, 2010 in U.S. Appl. No. 11/101,232, filed Dec. 10, 2004, Inventor: Robert J. Garabedian, (6 pages).

Appeal Brief dated Oct. 21, 2010 in U.S. Appl. No. 11/101,232, filed Dec. 10, 2004, Inventor: Robert J. Garabedian, (21 pages).

Notice of Allowance dated Dec. 23, 2010 in U.S. Appl. No. 11/101,232, filed Dec. 10, 2004, Inventor: Robert J. Garabedian, (8 pages).

* cited by examiner

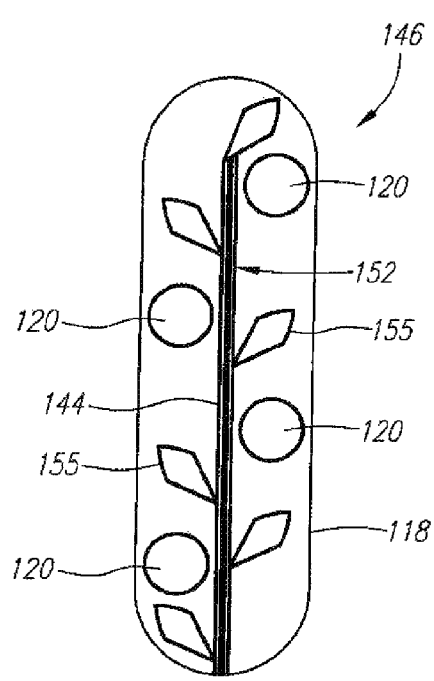
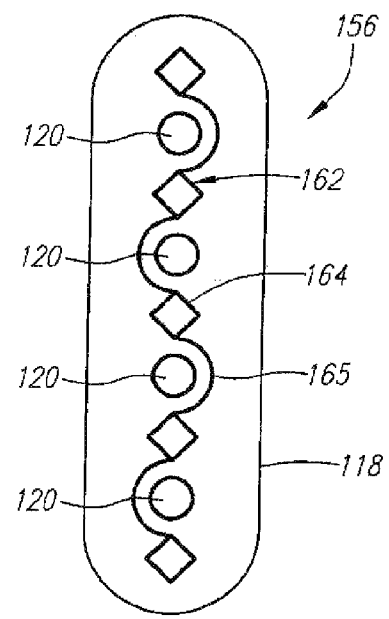
FIG. 10
FIG. 11
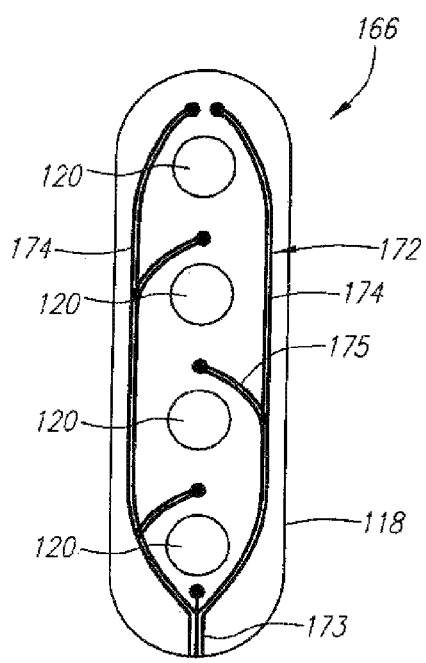
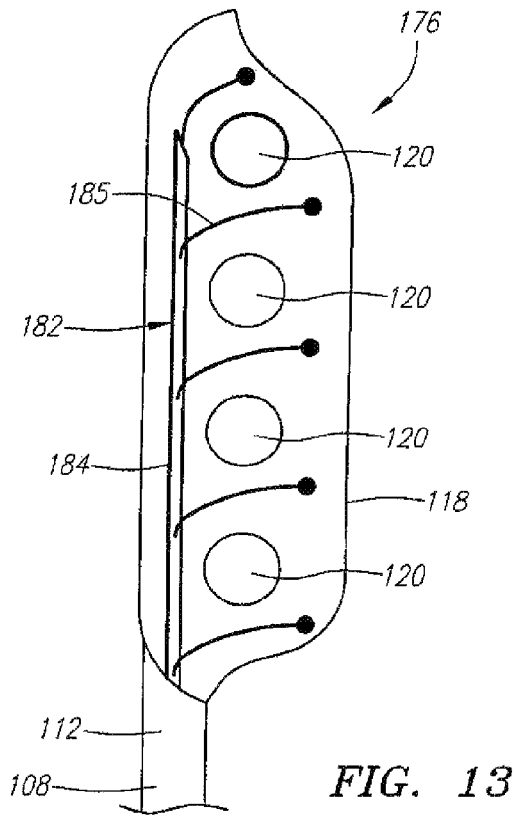
FIG. 12
FIG. 13

COLLAPSIBLE/EXPANDABLE TUBULAR ELECTRODE LEADS

RELATED APPLICATIONS

This application is a continuation of copending U.S. patent application Ser. No. 10/799,295, filed on Mar. 12, 2004, which is related to U.S. patent application Ser. No. 10/799,270, filed on Mar. 12, 2004, both of which are expressly incorporated herein by reference.

FIELD OF THE INVENTION

The invention relates to the implantation of electrode leads within a patient, and in particular, the implantation of stimulation electrode leads within a patient's spine to treat disorders, such as chronic pain.

BACKGROUND OF THE INVENTION

It is known to treat chronic pain by electrically stimulating the spinal cord, spinal nerve roots, and other nerve bundles. Although not fully understood, the application of electrical energy to particular regions of the spinal cord induces paresthesia (i.e., a subjective sensation of numbness or tingling) in the afflicted body regions associated with the stimulated spinal regions. This parasthesia effectively masks the transmission of chronic pain sensations from the afflicted body regions to the brain. Since each body region is associated with a particular spinal nerve root, it is important that stimulation be applied at the proper longitudinal position along the spinal cord to provide successful pain management and avoid stimulation of unaffected regions of the body. Also, because nerve fibers extend between the brain and the nerve roots along the same side of the spine as the body regions they control, it is equally important that stimulation be applied at the proper lateral position of the spinal cord. For example, to treat unilateral pain (i.e., pain sensed only on one side of the body), electrical stimulation is applied to the corresponding side of the spinal cord. To treat bilateral pain (i.e., pain sensed on both sides of the body), electrical stimulation is either applied directly to the midline of the spinal cord or applied to both lateral sides of the spinal cord.

In a typical procedure, one or more stimulation leads are introduced through the patient's back into the epidural space under fluoroscopy. The specific procedure used to implant the stimulation lead will ultimately depend on the type of stimulation lead used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the spinal cavity above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After the stimulation lead(s) (whether percutaneous or surgical) are placed at the target area of the spinal cord, the lead(s) are anchored in place, and the proximal ends of the lead(s), or alternatively lead extensions, are passed through a tunnel leading to a subcutaneous pocket (typically made in the patient's abdominal area) where a neurostimulator is implanted. The lead(s) are connected to the neurostimulator, which is then operated to test the effect of stimulation and adjust the parameters of the stimulation for optimal pain relief. During this procedure, the patient provides verbal feedback regarding the presence of paresthesia over the pain area. Based on this feedback, the lead position(s) may be adjusted and re-anchored if necessary. Any incisions are then closed to fully implant the system.

Various types of stimulation leads (both percutaneous and surgical), as well as stimulation sources and other components, for performing spinal cord stimulation are commercially available from Medtronic, Inc., located in Minneapolis, Minnesota, and Advanced Neuromodulation Systems, Inc., located in Plano, Tex.

The use of surgical leads provides several functional advantages over the use of percutaneous leads. For example, the paddle on a surgical lead has a greater footprint than that of a percutaneous lead. As a result, an implanted surgical lead is less apt to migrate from its optimum position than is an implanted percutaneous lead, thereby providing a more efficacious treatment and minimizing post operative procedures otherwise required to reposition the lead. As another example, the paddle of a surgical lead is insulated on one side. As a result, almost all of the stimulation energy is directed into the targeted neural tissue. The electrodes on the percutaneous leads, however, are entirely circumferentially exposed, so that much of the stimulation energy is directed away from the neural tissue. This ultimately translates into a lack of power efficiency, where percutaneous leads tend to exhaust a stimulator battery supply 25%-50% greater than that exhausted when surgical leads are used. As still another example, the multiple columns of electrodes on a surgical lead are well suited to address both unilateral and bilateral pain, where electrical energy may be administered using either column independently or administered using both columns.

Although surgical leads are functionally superior to percutaneous leads, there is one major drawback—surgical leads require painful surgery performed by a neurosurgeon, whereas percutaneous leads can be introduced into the epidural space minimally invasively by an anesthesiologist using local anesthesia.

There, thus, remains a need for a minimally invasive means of introducing stimulation leads within the spine of a patient, while preserving the functional advantages of a surgical lead.

SUMMARY OF THE INVENTION

In accordance with a first aspect of the present inventions, a medical lead is provided. The medical lead comprises an electrically insulative tubular membrane having an inner surface and an outer surface, a resilient spring element, and at least one electrode mounted. The spring element is associated with the membrane, e.g., by forming or mounting the spring element onto the membrane, or embedding the spring element into the membrane, and the electrode(s) is associated with the outer surface of the membrane, e.g., by forming or mounting the electrode(s) onto the outer surface, or embedding the spring element into the outer surface. The spring element can be associated with the inner surface or the outer surface of the insulative membrane.

The insulative membrane can be, e.g., continuous, porous, or meshed. The insulative membrane can take on a variety of tubular shapes. For example, the tubular shape can exhibit a circular, rectangular, triangular, or irregular geometry. In one embodiment, the insulative membrane is allowed to be flaccid and has a relatively low-stiffness, so that it can be made as thin as possible to facilitate collapsing of the medical lead into a low-profile geometry. The spring element is configured to expand the insulative membrane. The spring element can be, e.g., a discrete element or can be formed of a mesh or braid.

In one embodiment, the medical lead is configured to inhibit tissue growth. If associated with the inner surface of the insulative membrane, the spring element can be formed of any suitable resilient material, since it is not exposed to tissue. If associated with the outer surface of the insulative membrane, however, the spring element is preferably formed of a material that inhibits tissue growth. For example, in this case, the spring element can be formed of a continuous layer of material. In this manner, the implanted medical lead can be more easily retrieved from the patient's body, if necessary. The medical lead is preferably configured to be collapsed into a compact form for percutaneous delivery into the patient, thereby obviating the need to perform an invasive surgical procedure on the patient. The medical lead, when expanded, can be sized to fit within the epidural space of a patient.

In accordance with a second aspect of the present inventions, another medical lead is provided. The medical lead comprises a resilient tubular structure having a normally non-circular cross-sectional shape (e.g., a rectangle, oval, or crescent), and at least one electrode associated with the tubular structure. The tubular structure may comprise, e.g., a discrete element or can be formed of a mesh or braid. In one embodiment, the medical lead is configured to inhibit tissue growth. The medical lead is preferably configured to be collapsed into a compact form for percutaneous delivery into the patient, thereby obviating the need to perform an invasive surgical procedure on the patient. The medical lead, when expanded, can be sized to fit within the epidural space of a patient. In this case, the non-cylindrical geometry of the tubular structure allows the tubular structure to conform to the non-cylindrical shaped epidural space, so that, when expanded, painful tissue displacement is minimized.

In accordance with a third aspect of the present inventions, a method of treating a patient with one of the previously described medical leads is provided. The method comprises placing the medical lead into a collapsed state by applying a compressive force to the medical lead, percutaneously delivering the collapsed medical lead into the patient adjacent tissue to be treated, and placing the medical lead into an expanded state by releasing the compressive force. In one preferred method, the medical lead is used to stimulate tissue, such as spinal cord tissue.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 10 is a top view of yet another stimulation paddle that can be used in the kit of FIG. 1;

FIG. 11 is a top view of yet another stimulation paddle that can be used in the kit of FIG. 1;

FIG. 12 is a top view of yet another stimulation paddle that can be used in the kit of FIG. 1;

FIG. 13 is a top view of yet another stimulation paddle that can be used in the kit of FIG. 1;

DETAILED DESCRIPTION OF THE PREFERRED EMBODIMENTS

Figure 1:
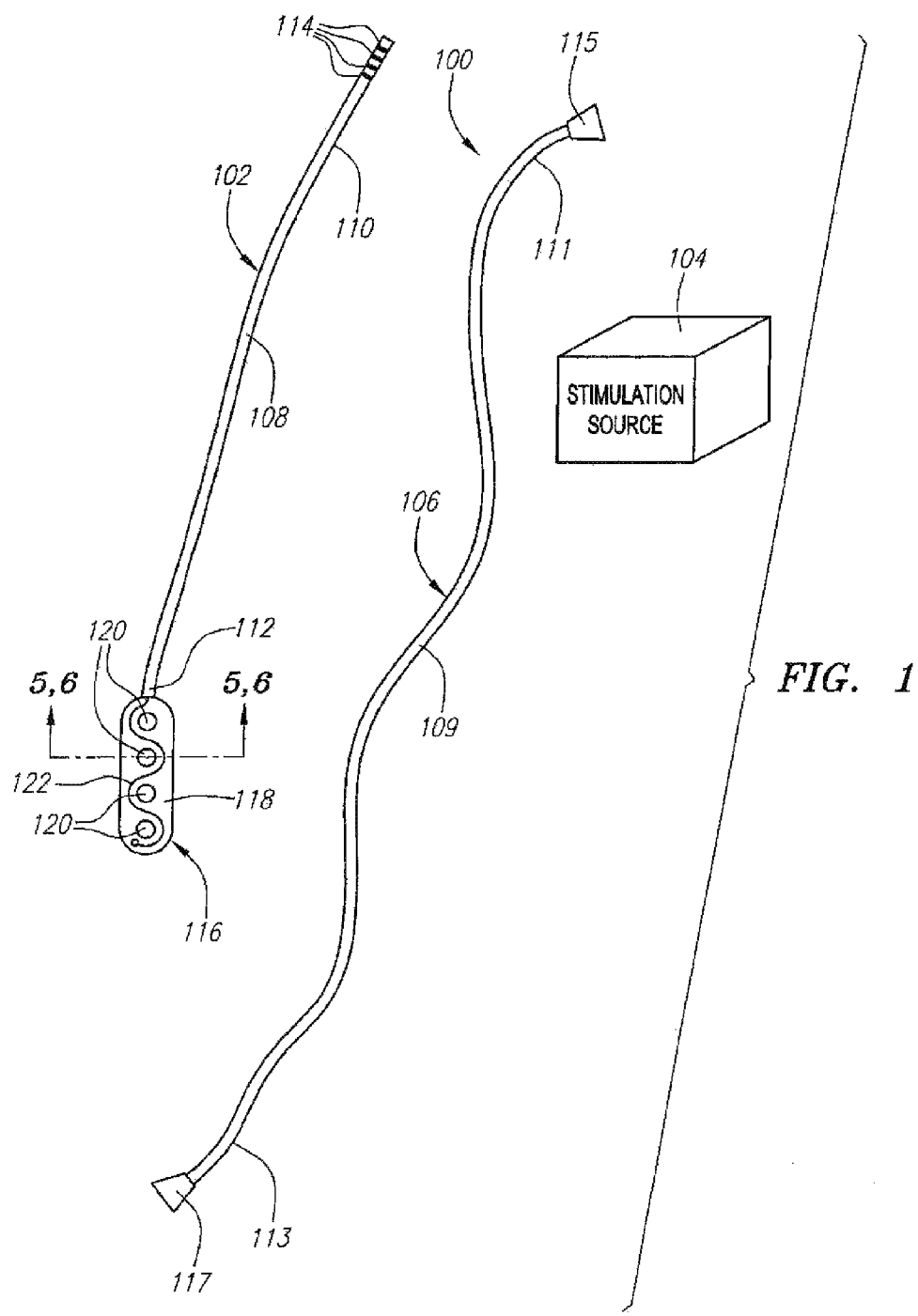
FIG. 1 is a plan view of a stimulation lead kit arranged in accordance with a preferred embodiment of the present invention.

Referring now to FIG. 1, a spinal cord stimulation lead kit 100 arranged in accordance with one preferred embodiment of the present invention is shown. In its simplest form, the stimulation kit 100 generally comprises a stimulation lead 102, which is configured to be percutaneously delivered and implanted into the epidural space of a patient's spine, an implantable electrical stimulation source 104 configured for delivering stimulation energy to the stimulation lead 102, and an optional extension lead 106 configured for connecting the stimulation lead 102 to the remotely implanted stimulation source 104.

It should be noted that although the kit 100 illustrated in FIG. 1 is described herein as being used in spinal cord stimulation (SCS) for the treatment of chronic pain, the kit 100, or a modification of the kit 100, can be used in an SCS procedure to treat other ailments, or can used in other applications other than SCS procedures, such as peripheral nervous system stimulation, sacral root stimulation, and brain tissue stimulation, including cortical and deep brain stimulation. In the latter case, the stimulation lead 102 can be delivered through a miniature cranial burr hole into the brain tissue.

The stimulation lead 102 comprises an elongated sheath body 108 having a proximal end 110 and a distal end 112. The sheath body 108 is composed of a suitably flexible material (such as polyurethane, silicone, etc.), which may either be resilient or non-resilient, and may be formed via an extrusion process or by any other suitable means. In the illustrated embodiment, the sheath body 108 is cylindrically-shaped and sized to fit through a Touhy-like needle (not shown). In this case, the diameter of the sheath body 108 is preferably less than 5 mm to allow it to be percutaneously introduced through a needle. More preferably, the diameter of the sheath body 108 is within the range of 1 mm to 3 mm, so that the stimulation lead 102, along with the secondary stimulation leads 104 described below, can comfortably fit within the epidural space of the patient. The sheath body 108 may have other cross-sectional geometries, such as oval, rectangular, triangular, etc. If rectangular, the width of the stimulation lead 102 can be up to 5 mm, since the width of an epidural space is greater than its height. The sheath body 108 may have an optional lumen (not shown) for receiving an obturator (not shown) that axially stiffens the sheath body 108 to facilitate percutaneous introduction of the stimulation lead 102 within the epidural space of the patient's spine, as will be described in further detail below.

The stimulation lead 102 further comprises a plurality of terminals 114 (in this case, four) mounted on the proximal end 110 of the sheath body 108. The terminals 114 are formed of ring-shaped elements composed of a suitable biocompatible metallic material, such as platinum, platinum/iridium, stainless steel, gold, or combinations or alloys of these materials, and can be mounted to the sheath body 108 in an interference fit arrangement.

Figure 2:
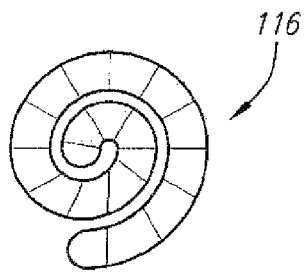
FIG. 2 is a cross-sectional view of a stimulation paddle used in the kit of FIG. 1, particularly shown in a low-profile collapsed geometry.
Figure 3:
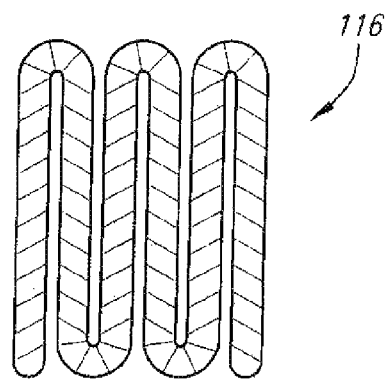
FIG. 3 is a cross-sectional view of the stimulation paddle used in the kit of FIG. 1, particularly shown in another low-profile collapsed geometry.
Figure 4:
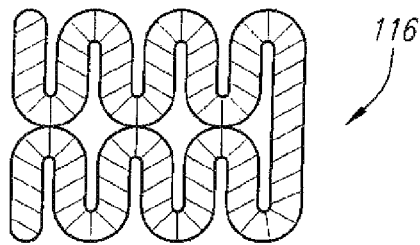
FIG. 4 is a cross-sectional view of the stimulation paddle used in the kit of FIG. 1, particularly shown in still another low-profile collapsed geometry.
Figure 5:
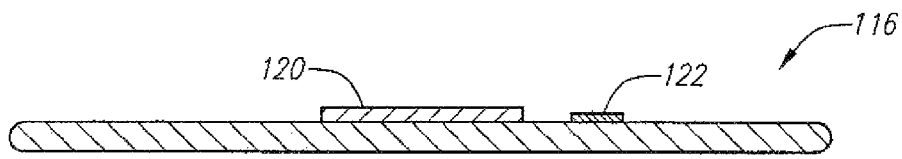
FIG. 5 is a cross-sectional view of a planar stimulation paddle that can be used in the kit of FIG. 1, taken along the line 5-5.
Figure 6:
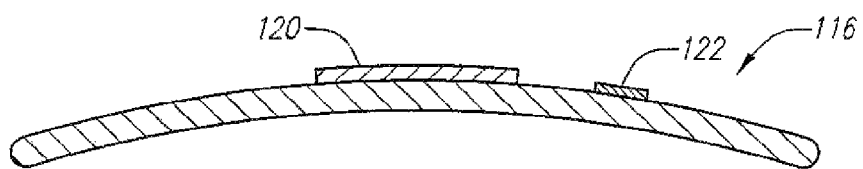
FIG. 6 is a cross-sectional view of a curviplanar stimulation paddle that can be used in the kit of FIG. 1, taken along the line 6-6.

The stimulation lead 102 further comprises a stimulation paddle 116 suitably mounted to the distal end 112 of the sheath body 108. In this embodiment, the stimulation paddle 116 is laterally centered on the sheath body 108 but as will be discussed below, the electrode paddle 116 can alternatively be laterally offset from the sheath body 108. As will be described in further detail below, the stimulation paddle 116 is configured to be placed into a compact, low-profile geometry by, e.g., rolling (see FIG. 2) or folding (see FIGS. 3 and 4) the paddle 116, and maintained in this low-profile geometry by applying a radial compressive force to the paddle 116, such as the force that would be applied by the lumen of a delivery device. Upon release of the radial compressive force, such as when the paddle 116 exits the delivery device, the paddle 116 springs open into its normally expanded geometry. In the illustrated embodiment, the paddle 116 expands into a planar geometry, as illustrated in FIG. 5. Alternatively, the paddle 116 can expand into a curviplanar geometry (i.e., a plane existing in three-dimensional space, e.g., a plane having an arcuate, curved, or undulating shape), as illustrated in FIG. 6.

Figure 7:
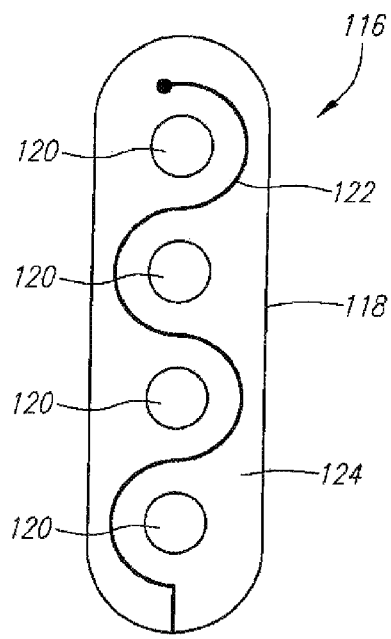
FIG. 7 is a top view of the stimulation paddle used in the kit of FIG. 1.

Referring further to FIG. 7, the stimulation paddle 116 comprises a paddle-shaped membrane 118 having a surface 124, an array of electrodes 120 mounted on the membrane surface 124, and a skeletal spring element 122 mounted on the membrane surface 124 between the electrodes 120. Alternatively, the electrodes 120 and skeletal spring element 122 can be respectively formed onto oppositely disposed surfaces of the membrane 118, so that the routing of the spring element 122 can be accomplished independently of the electrodes 120. To prevent or inhibit tissue growth after the stimulation lead 102 is implanted, the surface of the stimulation paddle 116 is preferably smooth and free of discontinuities that would otherwise be found in tissue growth exhibiting surfaces, such as mesh or braided material. In this manner, the implanted lead 102 can be more easily and percutaneously removed if necessary.

The electrodes 120 can be formed onto the membrane 118 using known deposition processes, such as sputtering, vapor deposition, ion beam deposition, electroplating over a deposited seed layer, or a combination of these processes. Alternatively, the electrodes 120 can be formed onto the membrane 118 as a thin sheet or foil of electrically conductive metal. Or, the electrodes 120 can be discrete elements that are embedded into the membrane 118, such that they lie flush with the surface 124 of the membrane 118. The electrodes 120 can be composed of the same electrically conductive and biocompatible material as the terminals 114, e.g., platinum, platinum/iridium, stainless steel, gold, or combinations or alloys of these materials. In the embodiment illustrated in FIG. 7, the electrodes 120 are arranged in a single column of four elements extending along the midline of the membrane 118. As will be described in further detail below, the electrodes 120 can have other configurations. In the illustrated embodiment, the electrodes 120 are circular, but can be formed as other geometric shapes, such as rectangular or ellipsoidal.

The stimulation lead 102 further comprises a plurality of conductors (not shown) extending through the sheath body 108 and membrane 118 and connecting each electrode 120 with a respective terminal 114. The conductors 122 are composed of a suitably electrically conductive material that exhibits the desired mechanical properties of low resistance, corrosion resistance, flexibility, and strength.

In the illustrated embodiment, the membrane 118 is composed of a continuous layer of material, although alternatively, the membrane 118 may be porous, meshed, or braided. Whether continuous or not, the material from which the membrane 118 is composed is relatively thin (e.g., 0.1 mm to 2 mm, although 1 mm or less is most preferred) and has a relatively low-stiffness. Exemplary materials are low-stiffness silicone, expanded polytetrafluoroethylene (ePTFE), or urethane. Due to these properties, the stimulation paddle 116 can be more easily collapsed into a low-profile geometry. For example, the stimulation paddle 116 can be rolled (see FIG. 2), or folded along one or more fold lines (see FIGS. 3 and 4). Although these properties allow the stimulation paddle 116 to be more easily collapsed into a low-profile geometry, thereby facilitating percutaneous delivery of the lead 102, these same properties also cause the membrane 118 to be too flaccid to easily spring open from the low-profile geometry. Radio-opaque markers (not shown) may optionally be provided on the membrane 118, so that the stimulation paddle 116 may be more easily navigated and placed into the epidural space of the patient under fluoroscopy.

The skeletal spring element 122, however, advantageously provides this necessary spring force. In particular, the spring element 122 is composed of a relatively high-stiffness and resilient material, such as stainless steel, a metallic and polymer material, or a high-stiffness urethane or silicone, that is shaped into a normally planar (curviplanar) geometry. In alternative embodiments, the spring element 122 may be composed of a shape memory material, such as nitinol, so that it assumes a planar (or curviplanar) geometry in the presence of a defined temperature, such as, e.g., body temperature. Thus, it can be appreciated that the normally planar (or curviplanar) geometry of the spring element 122 will cause the stimulation paddle 116 to likewise assume a planar (curviplanar) geometry in the absence of an external force (in particular, a compressive force). In the illustrated embodiment, the spring element 122 is formed of a thin layer of material that is laminated onto the membrane 118. In effect, the spring element 122 has a two-dimensional geometry in that it has a length and a width, but a minimal thickness. As a result, protrusions from the membrane 118 are avoided, thereby allowing the stimulation paddle 116 to be placed into a lower collapsed profile. Alternatively, the spring element 122 can be made from wire, which is cylindrical in nature, and thus, can be said to have a three-dimensional geometry. Whether formed from a layer of material or a wire, the spring element 122 may alternatively be embedded into the membrane 118, so that the surface of the spring element 122 is flush with the surface 124 of the membrane 118.

As can be seen in FIG. 7, the spring element 122 is formed of a single linear element that longitudinally extends along the membrane 118 in a meandering fashion between the electrodes 120. In this case, the laterally extending curves of the meandering spring element 122 act as cross-supports that provide the necessary spring force to urge the stimulation paddle 116 from its low-profile collapsed geometry into its expanded geometry. Notably, the end of the spring element 122 is beaded to prevent inadvertent perforation of the membrane 118 when the stimulation paddle 116 is mechanically stressed.

Figure 8:
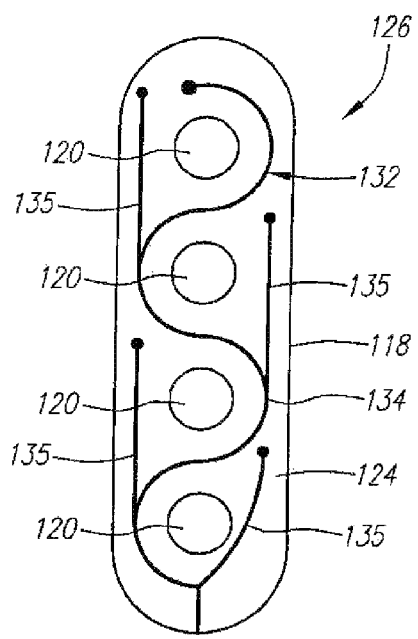
FIG. 8 is a top view of another stimulation paddle that can be used in the kit of FIG. 1.

The spring element 122 can have other geometries. For example, FIG. 8 illustrates a stimulation paddle 126 that comprises a skeletal spring element 132 that includes a main spring segment 134 that is similar to the spring element 122 illustrated in FIG. 7, and additional secondary spring segments 135 that extend longitudinally from the apexes of the main spring segment curves. The longitudinally extending secondary spring segments 135 provide additional axial stiffness to the stimulation paddle 126, thereby facilitating axial movement (i.e., the pushability) of the expanded stimulation paddle 126 by minimizing axial buckling of the membrane 118. To prevent inadvertent perforation of the insulative membrane 118, the distal ends of the secondary spring segments 135 are beaded.

Figure 9:
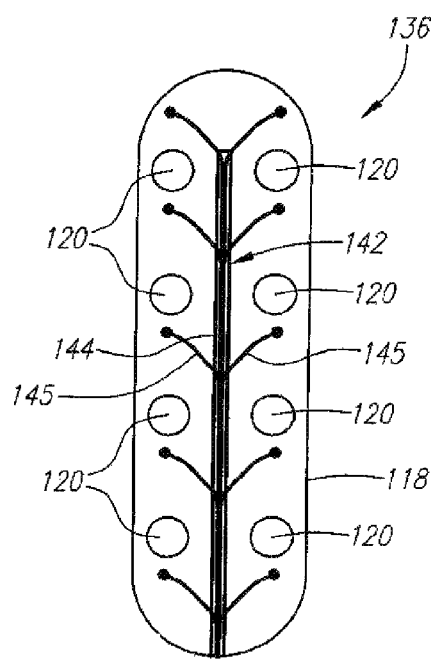
FIG. 9 is a top view of still another stimulation paddle that can be used in the kit of FIG. 1.

As another example, FIG. 9 illustrates a stimulation paddle 136 having a skeletal spring element 122 that includes a main spring segment 144 that extends longitudinally along the centerline of the membrane 118, and a plurality of lateral spring segments 145 that branch off of the main spring segment 144 between the electrodes 120. As can be seen in FIG. 9, the electrodes 120 are arranged as two columns of four elements each extending down the lateral sides of the membrane 118. Besides providing a structure from which the lateral spring segments 144 are supported, the main spring segment 144 provides axial stiffness to the stimulation paddle 146, thereby facilitating axial movement (i.e., the pushability) of the expanded stimulation paddle 146 by minimizing axial buckling of the membrane 118. To this end, the main spring segment 144 is somewhat wider than the lateral spring segments 145. The lateral spring segments 145 act as crossmembers that urge the membrane 118 into its normally expanded state, thereby providing the spring force that transforms the collapsed membrane 118 into the expanded geometry in the absence of a compressive force.

FIG. 10 illustrates a stimulation paddle 146 that comprises a skeletal spring element 152, which is similar to the previously described spring element 152, with the exception that it comprises lateral staggered spring segments 155 that are not linear, but are rather formed into two dimensional shapes—in this case a leaf shape. This increased size of the lateral spring segments 155 provides increased lateral spring force to the stimulation paddle 146. In this case, the number of lateral segments 155 are decreased, and the electrodes 120 are arranged into two columns of two elements each.

FIG. 11 illustrates a stimulation paddle 156 that comprises a skeletal spring element 162 with a plurality of diamond-shaped elements 164 longitudinally extending down the midline of the membrane 118 and a plurality of innerconnecting segments 165 between the respective diamond-shaped elements 164. The electrodes 120 are arranged in a single column of four electrodes 120 that extend down the midline of the membrane 118 between the respective diamond-shaped elements 164. The interconnecting segments 165 are curved in alternating left and right lateral directions in order to accommodate the centered electrodes 120.

FIG. 12 illustrates a stimulation paddle 166 that comprises a skeletal spring element 172 with a trunk segment 173, two main spring segments 174 that longitudinally extend from the trunk segment 173 along the left and right lateral sides of the membrane 118, and lateral spring segments 175 that branch off of the main spring segments 174 towards the midline of the membrane 118. Like the main spring segment 144 of the stimulation paddle 136 illustrated in FIG. 9, the main spring segments 174 provide axial rigidity to the stimulation paddle 166, while providing a structure supporting the lateral spring segments 175. Like the lateral spring segments 175 of the stimulation paddle 166 illustrated in FIG. 11, the lateral spring segments 175 act as cross members that facilitate transformation of the stimulation paddle 166 from its collapsed geometry into its expanded geometry. To prevent inadvertent perforation of the insulative membrane 118, the distal ends of the main spring segments 174 and secondary spring segments 175 are beaded. The electrodes 120 are arranged in a single column of four electrodes 120 extending down the midline of the membrane 118 between the respective secondary spring segments 175.

FIG. 13 illustrates a stimulation paddle 176 that comprises a membrane 118 that is laterally offset from the distal end 112 of the elongated sheath 108, and a skeletal spring element 182 with a main spring segment 184 that longitudinally extends along the membrane 118 and lateral spring segments 185 that laterally branch off from the main spring segment 184 towards the other lateral side of the membrane 118. The main spring segment 184 and lateral spring segments 185 function in the same manner as the main spring segment 144 and lateral spring segments 145 of the spring element 132 illustrated in FIG. 9. To prevent inadvertent perforation of the insulative membrane 118, the distal ends of the secondary spring segments 185 are beaded. The electrodes 120 are arranged in a single column of four elements that longitudinally extend down the midline of the membrane 118 between the lateral spring segments 185.

Although all of the stimulation paddles illustrated in FIGS. 7-13 have single spring elements, stimulation paddles with multiple spring elements can also be provided. In addition, tubular designs, which are, in effect, stimulation paddles that are wrapped around onto themselves, can be formed, in order to provide a more stable and snug engagement within the epidural space.

Figure 14:
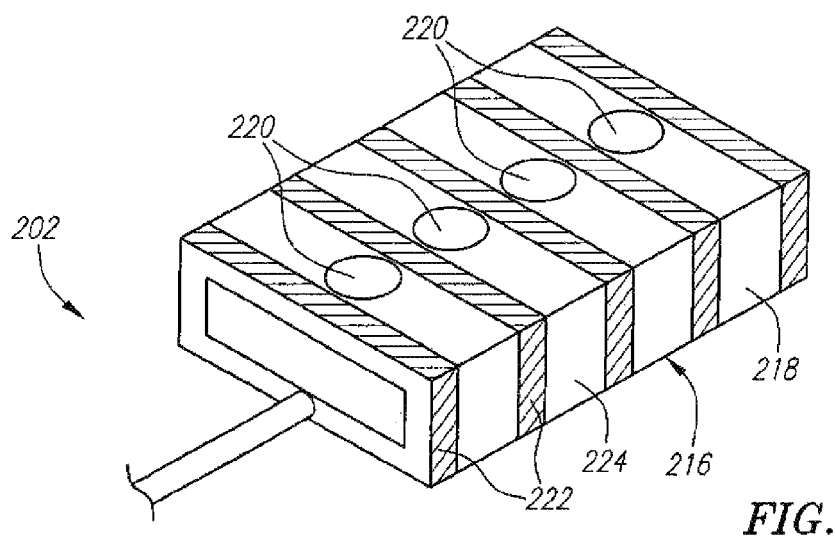
FIG. 14 is a perspective view of a stimulation tube that can be used in the kit of FIG. 1.
Figure 15:
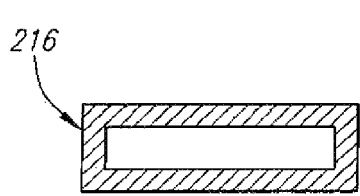
FIG. 15 is a cross-sectional view of the stimulation tube of FIG. 14, particularly showing its cross-sectional rectangle shape when placed in an expanded geometry.

In particular, FIGS. 14 and 15 illustrate a stimulation lead 202 that can alternatively be used in the kit 100 of FIG. 1. The stimulation lead 202 is similar to the stimulation 102 described above, with the exception that it comprises a stimulation tube 216, rather than a stimulation paddle. The stimulation tube 216 comprises a tubular, and specifically, rectangular cross-sectional shaped, membrane 218 having an outer surface 224, an array of electrodes 220 mounted on the outer surface 224, and skeletal spring elements 222 mounted on, the outer surface 224 between the electrodes 220. Alternatively, the electrodes 220 can be mounted on the outer surface 224, and the spring elements 222 can be mounted on an inner surface of the tubular membrane 218, so that the routing of the spring element 222 can be accomplished independently of the electrodes 220. To prevent or inhibit tissue growth after the stimulation lead 202 is implanted, the outer surface 224 of the stimulation tube 216 is preferably smooth and free of discontinuities that would otherwise be found in tissue growth exhibiting surfaces, such as mesh or braided material. In this manner, the implanted lead 202 can be more easily and percutaneously removed if necessary.

Figure 18:
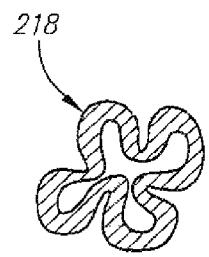
FIG. 18 is a cross-sectional view of the stimulation tube of FIG. 14, particularly shown in a low-profile collapsed geometry.

The electrodes 220 can be composed of the same material, shaped, and formed onto the membrane 218 in the same manner as the electrodes 120. In the embodiment illustrated in FIG. 14, the electrodes 220 are arranged in a single column of four elements longitudinally extending along one side of the membrane 218. Like the paddle membrane 118, the tubular membrane 218 is formed of a relatively thin (e.g., 0.1 mm to 2 mm, although 1 mm or less is most preferred), and is composed of a relatively low-stiffness material, such that it can be collapsed into a low-profile geometry, as shown in FIG. 18. Also, like the paddle membrane 118, the tubular membrane 218, by itself, is too flaccid to easily spring open from the low-profile geometry. Again, the skeletal spring elements 222 provide this necessary spring force, so that the stimulation tube 216 can expand outward in the absence of an external compressive force. The spring elements 222 can be composed of the same material and can be formed onto the membrane 218 in the same manner as the previously described spring element 122. In the embodiment illustrated in FIG. 14, each of the spring elements 222 extends around the circumference of the tubular membrane 218 in a meandering fashion. Of course, other spring element configurations can be used.

Figure 16:
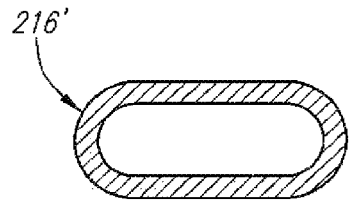
FIG. 16 is a cross-sectional view of an alternative stimulation tube, particularly showing its cross-sectional oval shape when palced in an expanded geometry.
Figure 17:
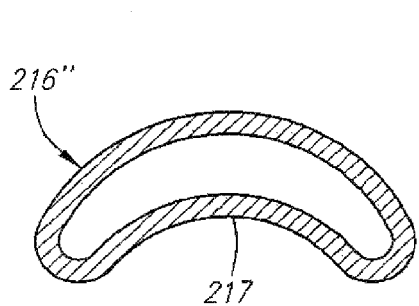
FIG. 17 is a cross-sectional view of another alternative stimulation tube, particularly showing its cross-sectional crescent shape when placed in an expanded geometry.

Although the membrane 218 is illustrated as having a normally expanded rectangular geometry, as best shown in FIG. 15, the membrane 218 can alternatively have other non-cylindrical tube-like shapes. For example, FIG. 16 illustrates an alternative tubular membrane 216' that has an oval cross-sectional shape, and FIG. 17 illustrates another tubular membrane 216" that has a crescent cross-sectional shape. The crescent-shaped tubular membrane 216" lends itself particularly well to spinal cord stimulation, since the spinal cord can be comfortably seated within a concave region 216 of the tubular membrane 216".

Figure 19:
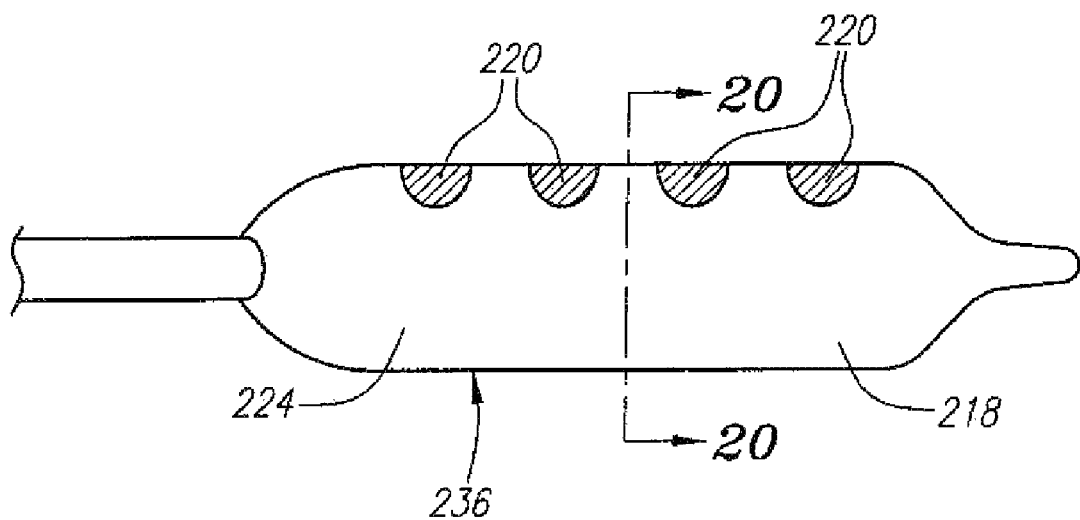
FIG. 19 is a perspective view of another stimulation tube that can be used in the kit of FIG. 1.
Figure 20:
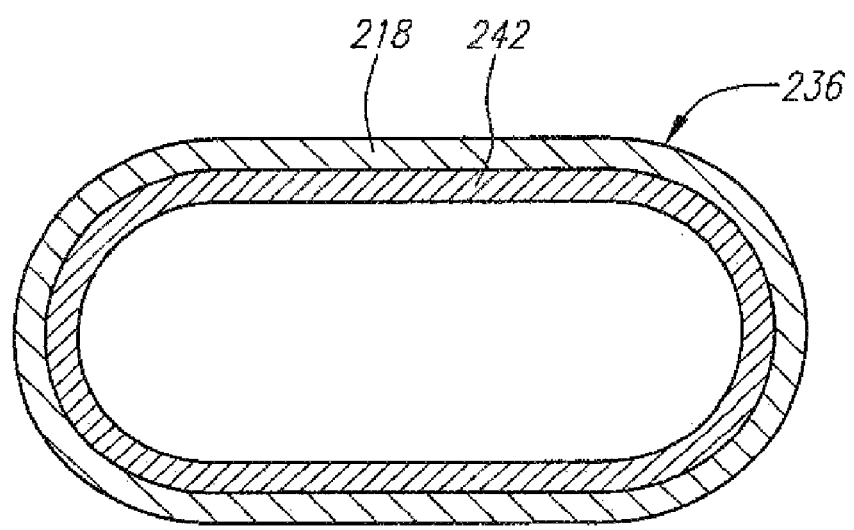
FIG. 20 is a cross-sectional view of the stimulation tube of FIG. 19, taken along the line 20-20.

FIGS. 19 and 20 illustrate another stimulation tube 236 that is similar to the stimulation tube 216, with the exception that, rather than having discrete spring elements, it comprises a resilient spring element 242 formed of a mesh or braid that may be composed of the same base material as the previously described spring elements. The tube 236 also has an oval cross-sectional shape, rather than a rectangular cross-sectional shape. The spring element 242 is formed on an inner surface of the tubular membrane 218, so that the mesh or braid material is not in contact with tissue, and therefore does not inhibit tissue growth. Like the spring element 222, the spring element 242 serves to urge the tubular membrane 218 from a low-profile collapsed geometry to an expanded geometry. As shown in FIG. 19, the distal and proximal ends of the stimulation tube 236 are tapered to allow for a safer deployment and, if necessary, retrieval of the device.

Referring back to FIG. 1, the implantable stimulation source 104 is designed to deliver electrical pulses to the stimulation lead 102 in accordance with programmed parameters. In the preferred embodiment, the stimulation source 104 is programmed to output electrical pulses having amplitudes varying from 0.1 to 20 volts, pulse widths varying from 0.02 to 1.5 milliseconds, and repetition rates varying from 2 to 2500 Hertz. In the illustrated embodiment, the stimulation source 104 takes the form of a totally self-contained generator, which once implanted, may be activated and controlled by an outside telemetry source, e.g., a small magnet. In this case, the pulse generator has an internal power source that limits the life of the pulse generator to a few years, and after the power source is expended, the pulse generator must be replaced. Generally, these types of stimulation sources 106 may be implanted within the chest or abdominal region beneath the skin of the patient.

Alternatively, the implantable stimulation source 104 may take the form of a passive receiver that receives radio frequency (RF) signals from an external transmitter worn by the patient. In this scenario, the life of the stimulation source 104 is virtually unlimited, since the stimulation signals originate from the external transmitter. Like the self-contained generators, the receivers of these types of stimulation sources 106 can be implanted within the chest or abdominal region beneath the skin of the patient. The receivers may also be suitable for implantation behind the ear of the patient, in which case, the external transmitter may be worn on the ear of the patient in a manner similar to that of a hearing aid. Stimulation sources, such as those just described, are commercially available from Advanced Neuromodulation Systems, Inc., located in Plano, Tex., and Medtronic, Inc., located in Minneapolis, Minn.

The optional extension lead 106 comprises an elongated sheath body 109 having a proximal end 111 and a distal end 113, much like the sheath body 108 of the stimulation lead 102, a proximal connector 115 coupled to the proximal end 113 of the sheath body 109, a distal connector 117 coupled to the distal end 111 of the sheath body 109, and a plurality of electrical conductors (not shown) extending through the sheath body 109 between the proximal and distal connectors 115/117. The length of the extension lead 102 is sufficient to extend from the spine of the patient, where the proximal end of the implanted stimulation lead 102 protrudes from to the implantation site of the stimulation source 104—typically somewhere in the chest or abdominal region. The proximal connector 115 is configured to be coupled with to the stimulation source 104, and the distal connector 117 is configured to mate with the proximal end of the stimulation lead 102.

Figure 21A:
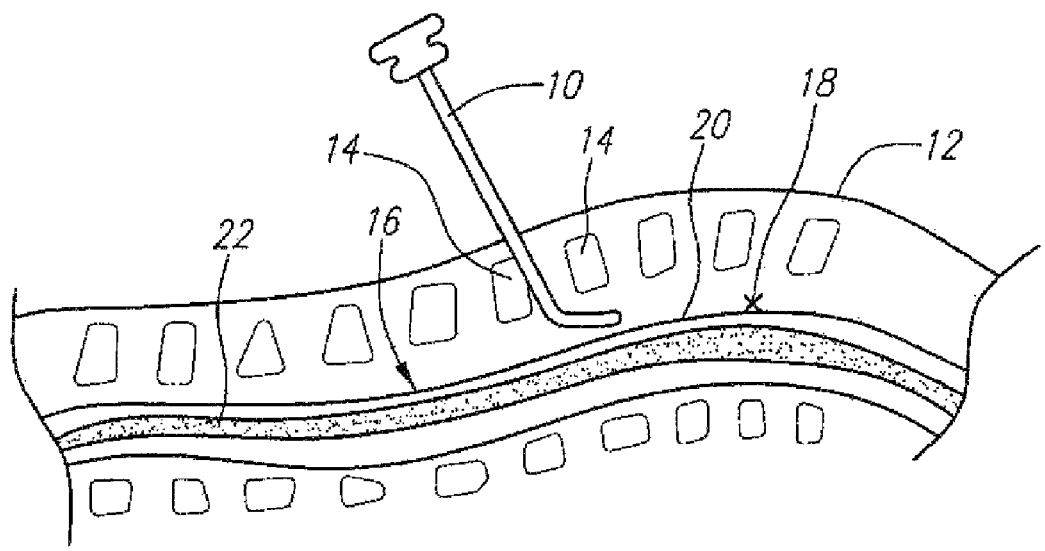
FIGS. 21A-21D are various views illustrating the installation of the kit of FIG. 1 into a patients spine.

Having described the stimulation lead kit 100, its installation and use in treating chronic pain will now be described with reference to FIGS. 21A-21D. After the patient has been prepared (which may involve testing the efficacy of spinal cord stimulation on the patient, and, once determining that the patient can be effectively treated with spinal cord stimulation, identifying and marking the appropriate vertebral intervals on the patient's skin and applying a local anesthetic to this region), a needle 10, such as, e.g., a Touhy needle, is inserted through the patient's skin 12 between the desired vertebrae 14, and into the epidural space 16 within the spine at a position inferior to target stimulation site 18 (FIG. 21A). In the illustrated method, the Touhy needle 10 will serve as the primary delivery mechanism for the stimulation lead 102. Alternatively, if an optional introducer (not shown) is used, a guide wire (not shown) is introduced through the needle 10 and advanced to or near the target stimulation site 18. The needle 10 is removed, the introducer is then introduced over the guide wire and advanced to the target stimulation site 18, and the guide wire is then withdrawn. In this case, the introducer will serve as the primary delivery mechanism for the stimulation lead 102.

Figure 21B:
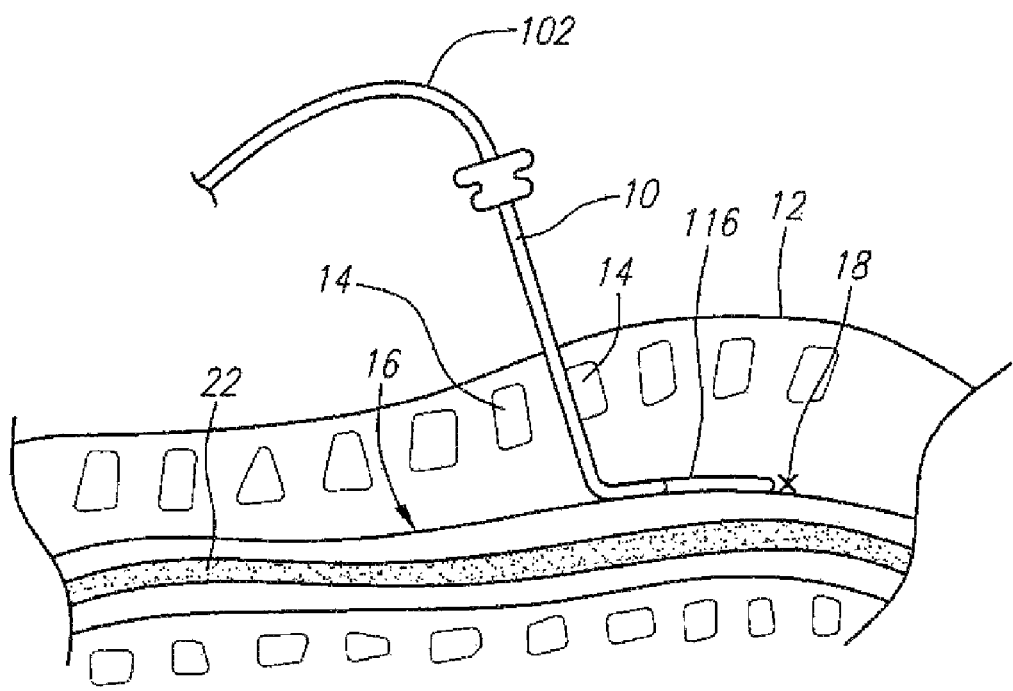
Figure 21C:
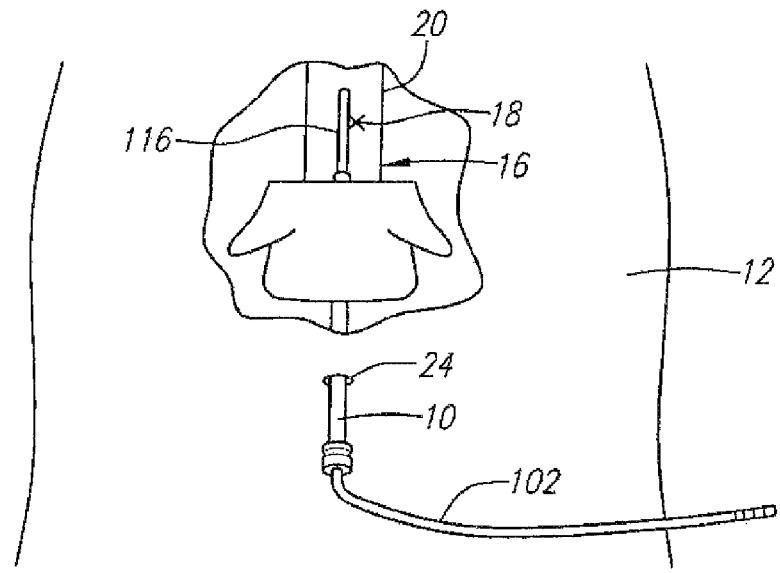
Figure 21D:
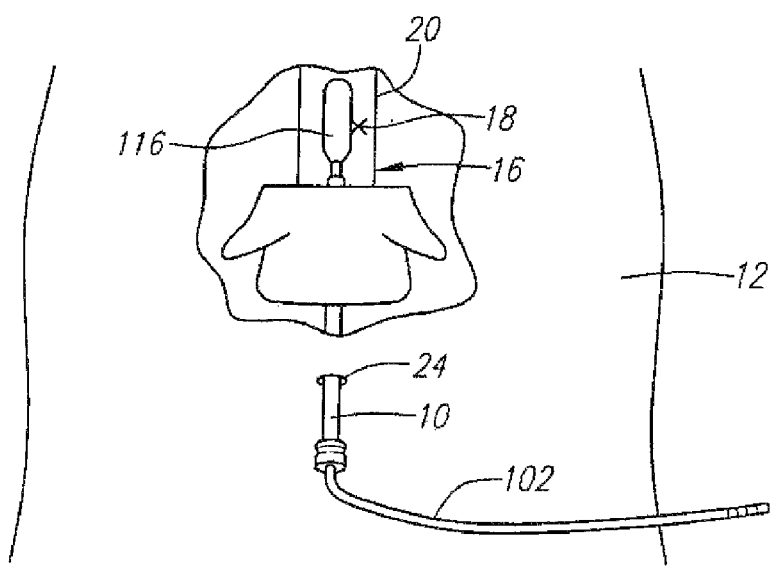

After the deliver mechanism is in place, the stimulation lead 102, with the stimulation paddle 116 collapsed into a low-profile geometry (see FIGS. 2-4), is then inserted through the needle or the introducer (whichever is in place), and positioned in the epidural space 16 at the target stimulation site 18 (FIGS. 21B and 21C). The stimulation tubes 216/236 can be inserted through the needle or the introducer in the same manner. If the stimulation lead 102 has an obturator lumen, an obturator can be used to provide additional axial stiffness and to facilitate control. Once the compressive radial force applied by the delivery device is released, the stimulation paddle 116 expands into its normally planar geometry, with the electrodes 120 facing the dural layer 20 and spanning the midline of the spinal cord 22 (FIG. 21D). If stimulation tubes 216/236 are used, their two-dimensional expansion will provide a more secure engagement within the epidural space. Notably, the use of non-cylindrical stimulation tubes, when expanded, conform better to the non-cylindrical epidural space 16, thereby minimizing painful tissue displacement.

Next, the needle 10 or introducer is removed, and the proximal end of the stimulation lead 102 is connected to a tester (not shown), which is then operated in a standard manner to confirm proper location of the stimulation lead 102 and to adjust the stimulation parameters for optimal pain relief. Once this optimization process has been completed, the tester is disconnected from the stimulation lead 102, which is then anchored in place using standard lead anchors (not shown). In the case of stimulation tubes 216/236, anchors may not be necessary, since they self-anchor themselves within the epidural space when expanded. Next, the stimulation lead 102 is coupled to the stimulation source 104 and implantation is completed (not shown). In particular, a subcutaneous pocket is created in the patients abdominal area for implantation of the stimulation source 104, and a tunnel is subcutaneously formed between the spine region and the subcutaneous pocket. The optional lead extension 106 is passed through the tunnel, after which the adapter 154 of the extension 106 is connected to the proximal end of the stimulation leads 102 and the connector 156 of the lead extension 106 is connected to the stimulation source 104. The stimulation source 104 is programmed and tested, and then placed within the subcutaneous pocket, after which all incisions are closed to effect implantation of the stimulation lead 102 and stimulation source 104. The stimulation source 104 can then be operated to convey stimulation energy from the stimulation source 104 to the electrodes 120 of the stimulation lead 102, where it is, in turn, conveyed into the neural tissue for pain relief.

It can be appreciated that the relatively large footprint made by the stimulation lead 102, much like a prior art surgical lead, provides a more stable platform for the electrodes 120. Also, like a prior art surgical lead, the electrodes 120 face in a single direction, thereby focusing the stimulation energy into the affected neural tissue where it is needed. Unlike a surgical lead, however, the stimulation lead 102 can be percutaneously delivered into the patient's spine in a minimally invasive and relatively pain-free manner, without requiring extensive patient recovery.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of treating a patient using a medical lead, the medical lead comprising an electrically insulative tubular membrane having an inner surface defining a lumen and an outer surface, a resilient spring element associated with the insulative membrane, and at least one electrode associated with the outer surface of the insulative membrane, the method comprising:
    placing the medical lead into a collapsed state by applying an external force to the tubular membrane of the medical lead to collapse the lumen;
    percutaneously delivering the collapsed medical lead into the patient adjacent spinal tissue to be treated; and
    placing the medical lead into an expanded state to locate the electrode in contact with the spinal tissue by releasing the compressive force from the tubular membrane to expand the lumen, whereby the resilient spring element facilitates expansion of the medical lead.

2. The method of claim 1, further comprising stimulating the spinal tissue with the medical lead.

3. The method of claim 1, wherein the insulative membrane has a normally non-cylindrical shape.

4. The method of claim 1, wherein the insulative membrane has a first stiffness, and the spring layer has a second stiffness greater than the first stiffness.

5. The method of claim 1, wherein the insulative membrane is flaccid.

6. The method of claim 1, wherein the spring element is a discrete element.

7. The method of claim 1, wherein the spring element is a mesh or braid.

8. The method of claim 1, wherein the spring element is configured to expand the insulative membrane.

9. The method of claim 1, wherein the resilient spring element is associated with the outer surface of the insulative membrane.

10. The medical lead of claim 1, wherein the resilient spring element is associated with the inner surface of the insulative membrane.

11. The method of claim 1, wherein the insulative membrane, spring element, and at least one electrode form a body that is configured to inhibit tissue growth.

12. The method of claim 1, wherein the medical lead is percutaneously delivered into the epidural space of the patient.

13. The method of claim 12, wherein the tubular structure comprises a discrete resilient spring element.

14. The method of claim 12, wherein the tubular structure comprises a resilient mesh or braid.

15. A method of treating a patient using a medical lead, the medical lead comprising a resilient tubular structure having a lumen and a normally non-circular cross-sectional shape, and at least one electrode associated with the tubular structure, the method comprising:
    placing the medical lead into a collapsed state by applying an external force to the tubular structure of the medical lead to collapse the lumen;
    percutaneously delivering the medical lead into the patient adjacent spinal tissue to be treated while the tubular structure is in the collapsed state; and
    placing the tubular structure of the medical lead into an expanded state to locate the electrode in contact with the spinal tissue by releasing the external force from the tubular structure to expand the lumen.

16. The method of claim 15, further comprising stimulating the spinal tissue with the medical lead.

17. The method of claim 15, wherein the non-circular shape is a rectangle.

18. The method of claim 15, wherein the non-circular shape is an oval.

19. The method of claim 15, wherein the non-circular shape is a crescent-shaped.

* * * * *